(12) United States Patent
Cohen

(10) Patent No.: US 6,235,528 B1
(45) Date of Patent: May 22, 2001

(54) ARTIFICIAL DIETS FOR ARTHROPODS

(75) Inventor: Allen C. Cohen, Starkville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/511,193

(22) Filed: Feb. 23, 2000

Related U.S. Application Data

(60) Provisional application No. 60/121,815, filed on Feb. 25, 1999.

(51) Int. Cl.$^7$ .............................. C12N 5/06; C12N 5/00; A01N 1/100; A01N 25/24; A01K 29/00

(52) U.S. Cl. ........................... 435/348; 435/1.1; 435/1.3; 435/390; 424/407; 119/1.6

(58) Field of Search .................................... 435/348, 260, 435/1.1, 390, 407, 1.3; 119/200, 204, 6.6; 424/407

(56) References Cited

U.S. PATENT DOCUMENTS

| | | | |
|---|---|---|---|
| 4,454,227 | 6/1984 | Röder | 435/240 |
| 5,834,177 | 11/1998 | Cohen | 435/1.1 |
| 5,945,271 | 8/1999 | Cohen | 435/1.1 |

FOREIGN PATENT DOCUMENTS

| | | | |
|---|---|---|---|
| 275815 | * 8/1990 | (CS) . | |
| 9807335 | 2/1998 | (WO) | A23L/3/34 |
| 9963814 | 12/1999 | (WO) | A01N/1/02 |

OTHER PUBLICATIONS

J.W. Debolt, "Meridic Diet for Rearing Successive Generations of *Lygus hesperus*," *Annals of the Entomological Society of America* 75:119–122 (1982).

J.W. Debolt, "Augmentation: Rearing, Release, and Evaluation of Plant Bug Parasites," in *Economic Importance and Biological Control of Lygus and Adelphocoris in North America*, Eds. R.C. Hedlund and H.M. Graham, United States Department of Agriculture–Agricultural Research Service ARS–64, 82–87 (1987).

J.W. Debolt, "Encapsulation of *Leiophron uniformis* by *Lygus lineolaris* and its Relationship to Host Acceptance Behavior," *Entomol, Exp. Appl.* 50:87–95 (1989).

S.A. Hassan and K.S. Hagen, "A New Artificial Diet for Rearing *Chrysopa carnea* larvae (Neuroptera, Chrysopidae)," *Zeitischrift fur Angewandte Entomologie* 86:315.320 (1978).

A.C. Cohen, "Simple Method for Rearing the Insect Predator *Geocoris punctipes* (*Heteroptera: Lygaeidae*) on a Meat Diet," *Journal of Economic Entomology*, 78:1173–1175 (1985).

S. Grenier, P.D. Greany, and A.C. Cohen, "Potential for Mass Release of Insect Parasitoids and Predators Through Development of Artificial Culture Techniques," in *Pest management in the Subtropics Biological Control—a Florida Perspective*, Intercept Ltd., P.O. Box 716, Andover, Hampshire, SP10 1YG UK, Chapter 10, pp. 181–205 1994.

A.C. Cohen and L.K. Smith, "A New Concept in Artificial Diets for *Chrysoperla rufilabris*: The Efficacy of Solid Diets," *Biological Control* 13:49–54 (1998).

E.S. Vanderzant, "Improvements in the Rearing Diet for *Chrysopa carnea* and the Amino Acid Requirements for Growth," *Journal of Economic Entomology*, 66(2):336–338 (1973).

M.G. Rojas, J.A. Morales–Ramos, and E.G. King, Two Meridic Diets for *Perillus bioculatus* (Heteroptera:Pentatomidae), a Predator of *Leptinotarsa decemlineata* (Coleoptera: Chrysomelidae), *Biological Control* 17:92–22 (2000).

A.C. Cohen. "Using a Systematic Approach to Develop Artificial Diets for Predators," in *Advances in Insect Rearing for Research and Pest Management*, Eds. T.E. Anderson and N.C. Leppla, Westview Press, Inc., Boulder, CO, Chapter 6, pp. 77–91 (1992).

A.C. Cohen, "Solid–to–Liquid Feeding: The Inside(s) Story of Extra–Oral Digestion in Predaceous Arthropoda," *American Entomologist* 103–116 (August 1998).

P. DeClercq, F. Merlevede, and L. Tirry, "Unnatural Prey and Artificial Diets for Rearing *Podisus maculiventris* (Heteroptera: Pentatomidae)," *Biological Control* 12:137–142 (1998).

P. DeClercq and D. Degheele, "A Meat–Based Diet for Rearing The Predatory Stinkbugs *Podisus maculiventris* and *Podisus sagitta* (Het.: Pentatomidae)," *Entomophaga* 37(1):149–157 (1992).

*Primary Examiner*—Leon B. Lankford, Jr.
*Assistant Examiner*—Michele C. Flood
(74) *Attorney, Agent, or Firm*—Margaret A. Connor; M. Howard Silverstein; John D. Fado

(57) ABSTRACT

Improved artificial diets or growth media are described which are suitable for rearing large numbers of viable and biologically fit arthropods, including zoophagous arthropods and phytophagous arthropods, including facultatively zoophagous arthropods. In a first embodiment, the growth medium is composed of a mixture of cooked egg, liquid, and carbohydrate source. In a second embodiment, the growth medium is composed of a plant-based phytophage diet which includes cooked egg yolk or cooked whole egg. In a third embodiment, the growth medium is composed of a mixture of cooked egg, liquid, and carbohydrate source in admixture with a plant-based phytophage diet which includes cooked egg yolk or cooked whole egg. The growth media are devoid of meat products or insect components and are suitable for mass production of arthropods at a reasonable cost for use in biological control programs or other biologically based technologies.

14 Claims, No Drawings

OTHER PUBLICATIONS

A.C. Cohen, D.A. Nordlund, and R.A. Smith, "Mass Rearing of Entomophageous Insects and Predaceous mites: are the Bottlenecks Biological, Engineering, Economic, or Cultural?," *Biocontrol News and Information* 20(3):85N–90N(1999).

J.L.D. Saavedra, J.C. Zanunico, R.N.C. Guedes & P. DeClercq, "Continous Rearing of *Podisus Nigrispinus* (Dallas) (Heteroptera: Pentatomidae) on an Artificial Diet," *Med Fac Landbouww, Univ Gent* 61(3a):767–772 (1995).

* cited by examiner

ARTIFICIAL DIETS FOR ARTHROPODS

CROSS-REFERENCE TO RELATED APPLICATIONS

This application claims the benefit of U.S. Provisional Application No. 60/121,815, filed Feb. 25, 1999. The disclosure of said provisional application is incorporated herein by reference in its entirety.

BACKGROUND OF THE INVENTION

1. Field of the Invention

The present invention relates to improved artificial diets or growth media for rearing arthropods, including zoophagous arthropods and phytophagous arthropods including facultatively zoophagous phytophages. The growth media of the invention are suitable for mass production of these insects at a reasonable cost for uses including as biological control agents.

2. Description of the Art

The phylum Arthropoda includes insects and arachnids. Within this phylum are zoophagous arthropods (those that eat animal materials), phytophagous arthropods (plant-eating arthropods), and facultatively entomophagous phytophages (plant-eating arthropods that display some animal material consumption in addition to eating plants).

In the United States and throughout the world, the application of synthetic chemical insecticides is the primary method of controlling arthropod pests of many agricultural commodities, including food, fiber, and ornamental crops. However, there is an increasing interest in reducing the use of chemical pesticides and fertilizers and to make agriculture more sustainable. Biological control is recognized as the best alternative to the use of chemical insecticides for controlling these pests.

Use of beneficial arthropod predators and parasites for biological control on a large scale as an alternative to pesticides depends on the ability to mass produce large quantities of viable and biologically fit arthropods at a reasonable cost. However, rearing of beneficial arthropods on their natural hosts/prey or on unnatural factitious hosts is too expensive to allow large scale use of beneficial arthropods in commercial agriculture. Accordingly, artificial diets or growth media are required for mass production at reasonable cost.

The phylum also includes destructive arthropods. For example, the western tarnished plant bug, *Lygus hesperus* Knight (Hemiptera: Miridae) and tarnished plant bug, *Lygus lineolaris* (Palisot de Beauvois) are very destructive pests, and their economic impact spans several cropping systems in North America (Hedlund and Graham, USDA Technical Bulletin ARS-64, 1987). Their impact is amplified by their remarkable ability to become resistant to pesticides and by their extremely broad host range (Hedlund and Graham, supra). Therefore, potential alternatives to conventional pesticides to control these pests have become very important. Such alternatives include development of biological control, biorational chemicals, plant breeding, sterile insect release, and genetic engineering. Development of management strategies based on these approaches would depend upon rearing systems that permit medium to large scale rearing of arthropod pests. A major component necessary for such rearing includes an inexpensive, high quality artificial diet that can be used to rear thousands to millions of the targeted pest (Cohen et al. 1999, *Biocontrol News and Information*, (accepted June, 1999); Nordlund, *Biocontrol News and Information* 17(2): 35–44,1999; Nordlund and Greenberg, *Biocontrol News and Information* 4:45–50, 1994).

A liquid diet for rearing *Lygus hesperus* which includes whole raw eggs was described by J. W. Debolt, *Annals of the Entomological Society of America* 75:119–122 (1982). The diet has been used successfully in rearing *L. hesperus* that were used for rearing both egg and nymphal parasitoids (Debolt, *U.S. Dept. Agric. Res. Serv.* (ARS-64), pages 82–87, 1987; Debolt, *Entomol. Exp. Appl.* 50:87–95, 1989). S. A. Hassan and K. S. Hagen, *Zeitschrift fur Angewandte Entomologie*, 86:315–320 (1978) describe liquid diets for rearing lacewings, *Chrysopa rufilabris* Stephens, larvae. Semi-solid meat-based artificial diets have been described for rearing *Geocoris punctipes* (Say) in publications by A. C. Cohen, *Journal of Economic Entomology*, 78:1173–1175 (1985); A. C. Cohen and N. M. Urias, *The Southwestern Entomologist*, 11:171–176 (1986); and A. C. Cohen and R. T. Staten in *Applications of Genetics to Arthropods of Biological Control Significance*, Eds. S. K. Narang et al., CRC Press, Inc., Chapter 7, pp. 121–132 (1994)). De Clercq et al. (*Entomophaga* 37:149–157 (1992)) describe an artificial insect diet for rearing the predatory stinkbugs *Podisus maculiventris* and *Podisus sagitta* using the meat-based diet of Cohen (1985) with added fresh (raw, liquid) egg yolk. Saavedra et al. (*Med Fac Landbouww Univ Gent* 61(3a):767–772 (1996) describe an artificial insect diet for *Podisus nigrispinus* based on the bovine meat diet developed by Cohen (1985, supra) having added bee's honey, brewer's yeast, fresh egg yolk, and Wesson's salt. An artificial meat paste-based diet containing cooked whole egg, which has been found suitable for mass rearing entomophages (predatory arthropods and parasitic insects) including big-eyed bugs, *Geocoris punctipes*, and lacewings, *Chrysoperla rufilabris*, has been described (A .C. Cohen, U.S. Pat. No. 5,834,177). Use of this meat paste-cooked egg diet was also found useful as a supplement for artificial diets for phytophagous pests that are known to supplement their plant-eating habits with some insect consumption (A. C. Cohen, U.S. Pat. No. 5,945,271).

SUMMARY OF THE INVENTION

The present invention is directed to improved artificial diets or growth media which are suitable for rearing large numbers of viable and biologically fit arthropods, including zoophagous arthropods and phytophagous arthropods, including facultatively zoophagous arthropods. The diets of the invention are free of insect components and meat products such as meat paste. Because the diets of the invention lack both insect components and meat products (such as meat paste), it was unexpected that they could be used so successfully to produce predatory arthropods and facultatively zoophagous phytophages. Prior art suggests that predatory and parasitic insects and mites require real arthropods or parts from arthropods or at least vertebrate-derived meat products in their immature stages of development.

In a first embodiment, the artificial growth medium is composed of a mixture of cooked egg, liquid, and carbohydrate source. Optional ingredients may be included as described in detail below and as illustrated in the examples. Preferably, the growth medium mixture is sufficiently blended so that the nutrients are substantially compositionally uniformly distributed. This diet is particularly suitable for providing nutrients in amounts and proportions effective to support growth of zoophagous arthropods.

In a second embodiment, the artificial growth medium is composed of a plant-based diet which includes cooked egg yolk or-cooked whole egg. Optional ingredients may be included as described in detail below and as illustrated in the examples. This diet is particularly suitable for providing nutrients in amounts and proportions effective to support growth of phytophagous arthropods, including facultatively zoophagous phytophages.

In a third embodiment, the growth medium of the first embodiment is used in combination with a plant-based diet which includes cooked egg yolk or cooked whole egg (growth medium of the second embodiment). Optional ingredients may be included as described in detail below and as illustrated in the examples. This diet is particularly suitable for providing nutrients in amounts and proportions effective to support growth of phytophagous arthropods, including facultatively zoophagous phytophages.

Because the diets of the three embodiments are devoid of both insect components and meat products (such as meat paste), they are less expensive to produce than previously developed comparable diets; simpler to prepare, and lend themselves more readily to prevention of microbial contamination than do previous diets, and thus find particular usefulness for the mass rearing of beneficial and destructive arthropods at a reasonable cost for subsequent uses, including as biological control agents.

Tests of the new diet of the first embodiment with larval green lacewings (*Chrysoperla rufilabris*) against a control diet described in U.S. Pat. No. 5,834,177 showed that the new diet produces similar quantities of adults of similar longevity rates, with slightly lower weights and numbers of eggs, at a significantly lower cost per kg of diet and with approximately half the labor time. The new diet (approx. $0.75/kg) and the previous medium (approx. $2.00/kg) have been shown to produce green lacewings of similar quality and quantity to insect (Ephestia) eggs, which cost about $300–500/kg.

As discussed in detail, below, the new diet of the third embodiment has been used to rear over fifteen generations of *L. hesperus* and is currently being used to support production colonies; it has also been used to rear *L. lineolaris* for five generations, thus far. This indicates the usefulness of the diet for producing high quality, vigorous phytophagous arthropods, including facultatively zoophagous arthropods, while reducing production costs.

The new diet of the third embodiment was compared to the Debolt (1982, supra) diet for rearing the facultatively zoophagous phytophage *Lygus hesperus*. Biological fitness estimates for *L. hesperus* indicated that mean biomass production per cage, adult wet and dry weights, survival to the adult stage, and egg production were significantly greater for the new diet than for the existing standard, Debolt (1982) diet. The ingredients in the diet of the third embodiment of the invention cost about ⅛ those in the complex (about 50 ingredients) Debolt diet, and preparation required less than ⅔ of the labor. The cost of diet for production per 1000 eggs was about $0.004 compared to $0.04 for an equal number of eggs from Debolt diet. The new diet further represents an improvement over the Debolt diet because it does not require expensive chemically defined items such as casein, linoleic acid, RNA, defined salts, or pure cholesterol. Instead, it comprises more nutritious components which are presented in a form much more suitable for the extra-oral digestion practiced by species of arthropods such as Lygus and all other Miridae, and nearly all Heteroptera—a slurry of solid materials, including cooked egg, that is blended with the plant components which include cooked egg.

Tests of the new diet of the third embodiment with *L. hesperus* against a control diet consisting of the phytophagous diet described in of U.S. Pat. No. 5,945,271, showed that the diet of the third embodiment was superior in terms of rates of development, dry weight, egg production, dry weight, and other fitness characteristics.

The diet of the third embodiment of the invention also supports development and reproduction in the tarnished plant bug, *L. lineolaris*. This is the first time the facultatively zoophagous phytophage *Lygus lineolaris* was produced for multiple generations using an artificial diet. This was entirely unexpected. Prior to this diet, this species had never been reared beyond a single generation on an artificial diet. It is an extremely difficult insect to colonize, and although it is of great economic and ecological importance as a destructive pest, it has never been reared, even on natural diets, in any substantial enough numbers to be used for biological control programs or other biologically based technologies. Efforts to rear this insect for the past 40 years using an artificial diet were unsuccessful. However, using the diet of the third embodiment of the invention, a colony of *L. lineolaris* is now being produced at a rate of about 50,000 adults/week, and there appears to be no biological limitation to the potential production of this species on this diet. Thus, the invention represents a major breakthrough in artificial diets for arthropods.

Millions of insects are required for augmentative biological control and other biologically based technologies. Obtaining such quantities demands the use of inexpensive diets to make moderate to large scale operations feasible. The growth media of the invention fulfills this need of providing an economical means for rearing arthropods. The invention also fulfills the need for large scale production of arthropods necessary for technologies such as sterile insect release, production of pathogens and parasitic insects using mass-produced arthropods as food.

Accordingly, the artificial growth media of the invention represent a major breakthrough for large-scale production of arthropods. Because of the high quality of arthropods produced, the lower price of the diets, and the greater ease of microbial decontamination, these diets have the potential to greatly expand the uses of arthropods in agriculture.

The media components are readily available. Further, the media of the invention can be readily packaged, for example in a membrane such as Parafilm®, for presentation to zoophagous arthropods, phytophagous arthropods or facultatively zoophagous phytophages. Additionally, the growth media can be readily freeze-dried, and can be used in the freeze-dried form or used after reconstitution with liquid. The use of freeze-drying (lyophilization) makes the diets easy to store, ship, or handle.

In accordance with this discovery, it is an object of the invention to provide improved artificial diets for production of arthropods, including zoophagous arthropods and phytophagous arthropods, including facultatively zoophagous phytophages.

Another object of the invention is to provide growth media for use for economical mass production of arthropods for subsequent release as biological control agents, for example, augmentative releases for control of populations of insect pests in commercial agriculture.

A further object of the invention is to provide artificial diets for economical large scale production of phytophagous and facultatively zoophagous phytophages for technologies such as sterile insect release, production of pathogens and parasitic insects using mass produced phytophages as food or for use in the production of phytophage products such as entomopathic fungi or entomopathic viruses.

A still further object of the invention is the provision of artificial diets for rearing arthropods which yield high quality predators.

An even still further object of the invention is the provision of artificial diets for rearing insects and other arthropods which are free of insect components and free of meat products.

Other objects and advantages of the invention will become readily apparent from the ensuing description.

DETAILED DESCRIPTION OF THE INVENTION

The present invention is directed to improved artificial diets or growth media suitable for rearing large numbers of viable and biologically fit zoophagous arthropods and phytophagous arthropods, including facultatively zoophagous phytophages.

In a first embodiment, the artificial growth medium is composed of a mixture of cooked egg, liquid, and carbohydrate source. Optional ingredients may be included as described in detail below and as illustrated in the examples. Preferably, the growth medium mixture is sufficiently blended so that the nutrients are substantially compositionally uniformly distributed. This diet is particularly suitable for providing nutrients in amounts and proportions effective to support growth of eggs, larvae, nymphs of zoophagous arthropods, and also provides nutrients effective for rearing zoophagous arthropods which have predaceous adult stages.

In a second embodiment, the artificial growth medium is composed a plant-based diet which includes cooked egg yolk or cooked whole egg. Optional ingredients may be included as described in detail below and as illustrated in the examples. This diet is particularly suitable for providing nutrients in amounts and proportions effective to support growth of phytophagous arthropods, including facultatively zoophagous phytophages.

In a third embodiment, the growth medium of the first embodiment is used in combination with a plant-based diet which includes cooked egg yolk or cooked whole egg (diet of the second embodiment). Optional ingredients may be included as described in detail below and as illustrated in the examples. This diet is particularly suitable for providing nutrients in amounts and proportions effective to support growth of phytophagous arthropods, including facultatively zoophagous phytophages.

The diets are essentially free of insect components, such as hemolymph, and are "meat-free," that is, they are essentially free of the edible flesh of animals, for example, the "meat paste" ingredient described in Cohen, 1985, supra, or the "protein-lipid paste" ingredient as described in U.S. Pat. No. 5,384,177 or 5,945,271, which patents are incorporated herein in their entirety. Illustrative of the "meat paste" ingredients described in U.S. Pat. No. 5,384,177 or 5,945,271 are blended ground beef and beef liver; meat and liver from other animals, such as chicken, lamb, and pork; fish innards; oysters; and cells derived from animals and propagated and multiplied using cloning technology. Because the diets of the invention are free of both insect components and meat paste, it was unexpected that it could be used so successfully to produce predatory arthropods, including predatory insects and facultatively zoophagous phytophages.

Further, because the diets of the invention are devoid of insect components and meat paste, they are useful for the production of arthropods on a commercial scale at a relatively low cost. A further advantage is that the diets lend themselves more readily to prevention of microbial contamination than do previous diets. Moreover, the arthropods are of sufficient quality to function effectively as biological control agents as described above.

As used herein, the term "zoophagous arthropods" refers to animals of the phylum Arthropoda that consume animal materials, for example, insects that feed on other insects. Exemplary of zoophagous arthropods are predatory and parasitic insects such as entomophages, and arachnids such as spiders, mites or ticks.

As used herein, the term "entomophages" refers to predatory arthropods and parasitic insects (parasitoids). Entomophages are discussed in detail in the text *Entomophagous Insects* by C. P. Clausen, Hafner Publishing Company, New York (1972), which is incorporated herein by reference. Entomophage refers to insects that feed upon other insects. These insects are broadly divided into two general classes, predators and parasitic insects. While there are many instances of species that are intermediate between the two general classes, a parasitic insect, in general, refers to one that, in its larval stage, develops either internally or externally upon a single host individual, the latter eventually dying as a result. The adults are generally free-living, and their food sources are usually distinct from those of the larvae. In contrast, a predator is generally free-living in the larval stage also and requires a number of individuals to provide food to grow to maturity. Clausen, supra, reports that there are 224 families in 15 orders, which to some extent, feed upon other insects.

Entomophages of particular importance to commercial agriculture are those useful as biological control agents, for example, through augmentative releases, to control populations of insect pests on agricultural commodities. Without being limited thereto, exemplary of predatory arthropods having importance for biocontrol in a commercial agricultural setting include predators of the Order (species)/family: Heteroptera: *Geocoris punctipes* (Say)/Lygaeidae [big eyed bug]; *Podisus maculiventris* (Say)/Pentatomidae; *Podisus sagitta* (Fab.)/Pentatomidae; *Macrolophus caliginosus* Wagner/Miridae; Neuroptera: *Chrysoperla carnea* Stephens/Chrysopidae [lacewings]; *Chrysopa sinica*/Chrysopidae; *Chrysopa scelestes* Banks/Chrysopidae; *Chrysopa lanata lanata* Banks/Chrysopidae; *Chrysopa septempunctata* Wesmael/Chrysopidae; Coleoptera: *Coleomegila maculata Harmonia axyridis*/Coccinellidae, *Olla abdominalis*/Coccinellidae. Without being limited thereto, exemplary parasitoids having potential importance for biocontrol in a commercial agricultural setting include Hymenoptera, in particular, Trichogrammatidae; Braconidae, and Ichneumonidae; and Diptera, in particular, Tachinidae.

Exemplary zoophagous arachnids include mites (family Phytoseiidae), and spiders (families Lycosidae, Thomisidae, Linyphiidae, Aranida).

As used herein, the term "phytophagous arthropods" refers to animals of the phylum Arthropoda that consume plants. Without being limited thereto, exemplary of phytophagous arthropods are Lepidoptera such as *Helicoverpa zea* (cotton bollworm), *Heliothis virescens* (tobacco budworm), *Spodoptera exigua* (beet armyworn) and other Spodoptera spp., e.g., *Trichoplusia ni* (cabbage looper), *Pseudoplusia includens* (soybean looper); Coleoptera such as Diabrotica spp., *Popillae japonica,* Epilachna spp.; various Curculionidae (weevils); Hemiptera/Heteroptera such as Lygus spp. (various Miridae), *Nezara viridula* (southern green stink bug), Euschistus spp.; phytophagous mites (Tetranychidae); Diptera such as *Delia platura*.

As used herein, the term "facultatively zoophagous phytophages" refers to phytophagous (plant-eating) arthropods that display some animal material consumption in addition to eating plants. [See, A. C. Cohen, "Plant feeding by Predatory Heteroptera: Evolutionary and Adaptational Aspects of Trophic Switching," pp. 1–17, 1996, In: *Zoophagous Heteroptera: Implications for Life History and Integrated Pest Management*, O. Alomar and R. N. Wiedenmann, eds. Thomas Say Publications in Entomology, 1996, and A. C. Cohen, "Biochemical and Morphological Dynamics and Predatory Feeding Habits in Terrestrial Heteroptera," pp. 21–32, In: *Predatory Heteroptera in Agroecosystems: Their Ecology and Use in Biological Control*, M. Coll and J. R. Ruberson, eds., Thomas Say Publications in Entomology. Entomological Society of America, Lanham, MD, 1998. ]

Without being limited hereto, exemplary of predominantly phytophagous insects that display some insect consumption in addition to eating plants, are Heteroptera: Miridae: Lygus spp., for example, *Lygus hesperus* Knight and *L. lineolaris*. Lygus spp. are known to be important pests in several cropping systems (seed alfalfa, cotton, strawberries, orchard crops). They are also known to supplement their plant-eating habits with some insect consumption. This fact (their facultative entomophagy) sets the stage for using the growth medium of the second and third embodiments for artificial diet-based production of parasites of phytophagous pests, for example, Lygus bugs. Mass rearing of phytophages is useful for other biocontrol purposes, for example to produce phytophage products such as entomopathic fungi or entomopathic viruses.

Diet of the First Embodiment

The artificial diet or growth medium of the first embodiment of the invention is composed of a mixture of cooked egg, liquid, and carbohydrate source. It is essentially free of insect components and meat paste, as discussed in detail, above. Optional ingredients as described below may be included.

Preparation of the diet is conveniently carried out by blending eggs during the cooking process with carbohydrate solution (liquid plus carbohydrate source) and one or more optional ingredients as desired. The blended egg ingredient in the mixture is cooked from a range of soft gel to hard texture. It is preferred that the egg is cooked to a soft, sticky solid, i.e., non-runny. It appears that this preferred scrambled egg consistency is more advantageous for arthropod production than hard-boiled egg consistency.

Preferably, the growth medium mixture is sufficiently blended so that the nutrients are substantially compositionally uniformly distributed.

The cooked egg ingredient can be provided by whole egg, by yolk and whole egg, by yolk and white, or by yolk alone. The eggs can be, for example, bird eggs such as chicken, turkey, duck, goose, quail, ostrich, or pheasant eggs.

Blended whole egg or blended egg yolk is advantageous for several reasons, including the following: (a) whole egg that is blended and cooked provides a concentrated amount of important nutrients such as cholesterol that do not separate during further handling of the medium, and the heating denatures avidin which otherwise binds biotin, an essential water soluble vitamin, (b) egg yolk provides an excellent natural source of cholesterol, lipids, lipoproteins, protein, and B-vitamins, (c) egg white provides proteins including albumin, (d) egg has hydrophilic and hydrophobic properties, and can retain nutrients by lipid-lipid interactions, protein-protein interactions, hydrophilic interactions, and by the formation of lipoprotein complexes, and (e) it may provide proteoglycans to act as natural cellular adherent materials. Additional egg yoke may also be added to the medium to increase lipoprotein availability.

The liquid component of the medium can comprise water, or other sources of water such as milk, medium from tissue culture or aqueous plant extracts, and may include additional water soluble nutrients or additives such as vitamins, minerals, antimicrobial agents, or preservatives. The liquid functions to support growth of an arthropod, and further, in the case of entomophages that feed using extra-oral digestion, provides liquid for entomophages to pre-digest their food.

The carbohydrate source of the medium can comprise sucrose, plant starch such as corn, potato, wheat, rice, or barley starch, high fructose corn syrup, honey, other plant sugars or animal glycogen or other sugars such as glucose or other monosaccharides; lactose, trehalose or other disaccharides; oligosaccharides or polysaccharides as known to those of skill in the art or combinations thereof Optionally, glycerol and/or proline or equivalents thereof can be added to the carbohydrate solution as microbial inhibitors.

Other optional adjuvants or supplements may also be incorporated into the medium to enhance the growth of the target arthropod or prevent the growth of microbial contaminants. For example, the growth medium may also include other nutrients, for example, lipids (with or without emulsifying agents) such as plant oils, e.g., corn oil, safflower oil, soybean oil or animal fats such as lard, purified amino acids, and nucleic acids. These nutrients may also have important metabolic and behavior-inducing characteristics, such as phagostimulatory nutrients, that is, an ingredient that stimulates the target arthropod to stimulate the complete feeding response. Exemplary of phagostimulant sources are sucrose, honey, tryptophan, and gamma amino butyric acid.

Optionally, a multivitamin mixture, e.g., Vanderzant vitamin mixture (see E. S. Vanderzant, "Rearing Lygus Bugs on Artificial Diets," *Journal of Economic Entomology* 60: 813–816, 1967), other sources of vitamins, or sources of B-vitamins, e.g., brewer's yeast, torula yeast, may be added to supplement vitamins in the growth medium. Yeast is also a source of nitrogen, amino acids, and trace elements.

Further optional ingredients include preservatives and/or antimicrobial agents. Without being limited thereto, exemplary of such agents are formalin, propionate, potassium sorbate, streptomycin, and chlortetracycline. The antimicrobial agents are included, individually or in combination, in an amount sufficient to prevent growth of microbial contaminants, but insufficient to prevent growth of the target arthropod.

An exemplary formulation is described in detail in Example 1, below. In brief, cooked eggs are blended during the cooking process with sugar solution and honey and stirred with acetic acid and brewer's yeast. Acetic acid is useful as a food acid for adjusting the pH, and also in helping solidify the egg and help it remain sticky and adherent.

The growth medium provides nutrients in amounts and proportions effective to support growth of zoophagous arthropods, and as discussed in detail, below, in the third embodiment, when used in combination with a plant based diet which includes cooked egg yolk or cooked whole egg, it provides nutrients in amounts and proportions effective to support growth of phytophagous arthropods including facultatively zoophagous phytophages.

In each of the first, second, and third embodiments, the growth medium should contain essential nutrients. Essential nutrients are defined as those nutrients such as minerals, amino acids, cholesterol, fatty acids, lipid soluble vitamins, and water soluble vitamins that are essential to the growth of the target arthropod. This can be readily determined for any circumstance. For instance, the basic nutritional requirements of parasitoids and predators for an artificial growth medium are discussed in S. Grenier et al. in *Pest Management in the Subtropics, Biological Control—a Florida Perspective,* Eds. D., Rosen, F. D. Bennett, and J. L. Capinera, Intercept Press, Andover, U.K., Chapter 10, pp. 181–205 (1994), which is incorporated herein by reference. As known to those in the art, nutrients essential for growth of an arthropod can vary among species. For any particular target arthropod, nutrients essential for growth can readily be determined by procedures known to those of skill in the art, for example, dietary deletion. The actual concentrations selected may be determined by the practitioner skilled in the art.

An advantageous feature of diets of the first, second, and third embodiments is that although supplements of vitamins, and preservatives may be added, the diets may be prepared without supplements of defined chemicals such as purified proteins; RNA; purified lipids, e.g., triglyceride, trilinoleic acid; purified salts; or purified amino acids.

In general, when the diet of the first embodiment is used for the production of zoophagous arthropods, the amount of the protein in the growth medium, that is, the combined amount of all protein or combination of amino acids and protein in the medium should be approximately 5–20% of growth medium (total wet weight), the amount of the fat should be about 4–15% of the growth medium (total wet weight), the amount of carbohydrate should be about 3–20% of the growth medium (total wet weight), the amount of cholesterol should be in the range of approximately 250–3000 mg per kg growth medium and the amount of liquid in the growth medium (including added liquid and liquid contained in the other ingredients) should be in the range of about 55–80% of the growth medium (total wet weight). The fat and protein sources may be provided in combination such as by lipoproteins.

In general, when the diet of the first embodiment is used for the production of zoophagous arthropods, the pH of the growth medium can range from about 4.0 to 8.0. It is recommended that the pH of the growth medium for use in rearing entomophages be in the range of approximately pH 5.5 to 7. 4. The pH can be conveniently adjusted using a solution of acetic acid or potassium hydroxide.

The medium of the first, second or third embodiment can be readily packaged, for example, in a membrane such as Parafilm® (a flexible, moldable, self-sealing, odorless, moisture resistant, thermoplastic, semi-transparent, and practically colorless membrane), and be presented to the insects in a shape and wall thickness that simulates natural prey or natural plant materials. The packaged medium can be sterilized or pasteurized to have a longer shelf life for subsequent use for rearing the target arthropod. The growth medium can be readily freeze-dried can be used in the freeze-dried form or used after reconstitution with liquid. The use of freeze-drying (lyophilization) makes the diet easy to store, ship, or handle.

Techniques for rearing arthropods in vitro on artificial diets have been described by Cohen et al., 1985, supra, which is incorporated herein by reference and in U.S. Pat. Nos. 5,834,177, and 5,945,271, which are incorporated herein be reference in their entirety. For example, eggs, larvae, nymphs or adults with predacious stages are provided with the growth medium in an amount effective to support growth, and incubated under conditions and for a period of time for the eggs or larvae to mature into pupae or adults, for nymphs to mature into adults and for the adults to advance through reproductive stages. Preferably, the growth medium is presented in a suitable container such as a petri dish or multicell container. Organdy may be used to enclose cells to permit air flow and prevent escapes. Because of the mobility of first and second instar larvae of zoophagous arthropods and their predisposition for cannibalism, multi-cell or other compartmentalized containers are preferred to segregate developing larvae. The cells and/or diet may be covered with a membrane. The membrane covers may be formed from a variety of polymeric materials, including but not limited to paraffin, polyethylene, polypropylene, and Parafilm®. Use of Parafilm® as a cover is particularly advantageous as this membrane may serve as a phagostimulant, and it keeps the diet from drying out and from being accessed by microbes. I have found that presentation of the medium in stretched Parafilm® membrane is advantageous for the smaller predators so the mouthparts of the insect can readily penetrate the Parafilm®.

Diet of the Second Embodiment

The artificial diet or growth medium of the second embodiment of the invention comprises a plant-based diet which includes cooked egg yolk or cooked whole egg. Optional ingredients may be included as described in detail below and as illustrated in Example 2 (see Components B and C). This diet is particularly suitable for providing nutrients in amounts and proportions effective to support growth of phytophagous arthropods, including facultatively zoophagous phytophages.

Plant materials for insect rearing are described in *Handbook of insect Rearing,* P. Singh and R. F. Moore, Elsevier Press, Amsterdam, Volumes I and II, 1985, 488 and 514 pages, which are herein incorporated by reference. Without being limited thereto, exemplary sources of plant materials for the diet include beans, grains, seeds or nuts, ground or blended. This includes meal from wheat, soy, corn, rice, barley, oats, buckwheat, various beans and peas (e.g., legumes such as navy beans, pinto beans, mung beans), nut flours (peanuts, cashews, macadamias), plant seeds (e.g. sunflower seeds).

A critical feature is that the artificial diet or growth medium include added cooked egg yolk or cooked whole egg. Conveniently, this is carried out by adding fresh egg yolk or fresh whole egg to the plant-based diet and autoclaving or flash sterilizing the mixture. Other preparation procedures are within the skill of the art.

This plant-based, cooked egg diet also includes liquid. As with the diet of the first embodiment, the liquid can comprise water, or other sources of water such as milk, medium from tissue culture or aqueous plant extracts, and may include additional water soluble nutrients or additives such as vitamins, minerals, antimicrobial agents, or preservatives.

Other adjuvants or supplements may also be incorporated into the medium to enhance the growth of the target arthropod or prevent the growth of microbial contaminants. For example, the growth medium may also include other nutrients, for example, purified amino acids, nucleic acids, and/or lipids (with or without emulsifying agents) such as plant oils, e.g., corn oil, safflower oil, soybean oil or animal fats such as lard. These nutrients may also have important metabolic and behavior-inducing characteristics, such as phagostimulatory nutrients, that is, an ingredient that stimulates the target arthropod to stimulate the complete feeding response.

A multivitamin mixture, e.g., Vanderzant vitamin mixture, other sources of vitamins, or sources of B-vitamins, may be added to supplement vitamins in the growth medium.

Preservatives and/or antimicrobial agents as discussed in detail above may also be included in the diet as desired.

Components B and C of Example 2, below, illustrate an exemplary formulation of the second embodiment of the invention. Component B is prepared by mixing together sources of plant materials, liquid, and egg yolk or whole egg, and autoclaving and cooling the mixture. Component C is prepared by mixing together liquid, a vitamin mix, and optionally a preservative and/or antimicrobial agent as desired. Next, Component C is added to cooled Component B, and the mixture is blended. The combination of Components B plus C comprises the diet of the second embodiment.

The diet is a stiff (non-runny) slurry composed of a range of particles from about 1 to 1000 µm. The diet comprises approximately 55–85% liquid and 15–45% plant diet plus cooked egg. Preferably, the amount of the protein in the growth medium, that is, the combined amount of all protein in the medium should be approximately 3–15% of growth medium (total wet weight), the amount of the lipid should be about 1–10% of the growth medium (total wet weight), the amount of carbohydrate should be about 5–30% of the growth medium (total wet weight), and the amount of liquid in the growth medium (including added liquid and liquid contained in the other ingredients) should be in the range of about 55–85% of the growth medium (total wet weight). The fat and protein sources may be provided in combination such as by lipoproteins. The mixture may be supplemented with pure vitamins (about 0.01% to 0.1% of the total diet) or with 1–5% vitamins (which include sugar filler).

The pH of the medium can range from about 4.0 to 8.0. A preferred pH range is about 4.8 to 6.8.

Water activity of the growth medium of the second embodiment is about 0.800 to 0.995, preferably about 0.90 to 0.99. Viscosity can be anything from a loose slurry (such as pourable Cream of Wheat® or oatmeal) to a stiff slurry such as oatmeal that cannot be poured and does not seek its own level in a container). A preferred mixture is one that is a stiff slurry that can, with pressure, fill a container.

The medium can be readily packaged, for example in a membrane such as Parafilm®, as described in detail above. The packaged medium can be sterilized or pasteurized. The growth medium can be readily freeze-dried and can be used in the freeze-dried form or used after reconstitution with liquid. Techniques for rearing phytophagous arthropods including facultatively zoophagous arthropods are as described above.

Diet of the Third Embodiment

The artificial diet or growth medium of the third embodiment of the invention comprises the growth medium of the first embodiment in combination with a plant-based diet which includes cooked egg yolk or cooked whole egg (diet of the second embodiment of the invention). Optional ingredients may be included as described herein and as illustrated in the examples. This diet is particularly suitable for providing nutrients in amounts and proportions effective to support growth of phytophagous arthropods, including facultatively zoophagous phytophages.

In brief, preparation of the diet is carried out by mixing together (a) a plant-based diet of phytophagous insects which includes cooked egg yolk or cooked whole egg (95–80% by weight) with (b) 5–20% (by weight) of the growth medium of the first embodiment of the invention.

Plant materials for insect rearing are as described above. A critical feature is that the plant-based portion of the diet include added cooked egg yolk or cooked whole egg. Conveniently, this is carried out by adding fresh egg yolk or fresh whole egg to the plant-based portion and autoclaving or flash sterilizing the mixture.

Other adjuvants or supplements may also be incorporated into the medium to enhance the growth of the target arthropod or prevent the growth of microbial contaminants. For example, the growth medium may also include other nutrients, for example, purified amino acids, nucleic acids, and/or lipids (with or without emulsifying agents) such as plant oils, e.g., corn oil, safflower oil, soybean oil or animal fats such as lard. These nutrients may also have important metabolic and behavior-inducing characteristics, such as phagostimulatory nutrients, that is, an ingredient that stimulates the target arthropod to stimulate the complete feeding response.

A multivitamin mixture, e.g., Vanderzant vitamin mixture, other sources of vitamins, or sources of B-vitamins, may be added to supplement vitamins in the growth medium.

Preservatives and/or antimicrobial agents as discussed in detail above may also be included in the diet as desired.

An exemplary formulation is described in detail, below, in Example 2. In brief, a preferred formulation and preparation procedure are as follows:

Component A is prepared which comprises the diet of the first embodiment. Component B is prepared by mixing together sources of plant materials, liquid, and egg yolk or whole egg, and autoclaving and cooling the mixture. Component C is prepared by mixing together liquid, a vitamin mix, and optionally a preservative and/or antimicrobial agent as desired. Next, Component C and Component A are added to Component B and the mixture is blended. The combination of Components A plus B plus C comprise the diet of the third embodiment.

The diet is a stiff (non-runny) slurry composed of a range of particles from about 1 to 1000 µm. Preferably, the amount of the protein in the growth medium, that is, the combined amount of all protein in the medium should be approximately 3–15% of growth medium (total wet weight), the amount of the lipid should be about 1–10% of the growth medium (total wet weight), the amount of carbohydrate should be about 5–30% of the growth medium (total wet weight), and the amount of liquid in the growth medium (including added liquid and liquid contained in the other ingredients) should be in the range of about 55–85% of the growth medium (total wet weight). The fat and protein sources may be provided in combination such as by lipoproteins. As with the second embodiment, the mixture may be supplemented with pure vitamins (ca. 0.01% to 0.1% of the total diet) or with 1–5% vitamins (which include sugar filler).

The pH of the medium can range from about 4.0 to 8.0. A preferred pH range is about 4.8 to 6.8. A pH of 5.8 produced superior results for rearing Lygus as shown in Example 2, below.

Water activity of the growth medium of the third embodiment is about 0.800 to 0.995, preferably about 0.90 to 0.99. Viscosity can be anything from a loose slurry (such as pourable Cream of Wheat® or oatmeal) to a stiff slurry such as oatmeal that cannot be poured and does not seek its own level in a container). A preferred mixture is one that is a stiff slurry that can, with pressure, fill a container.

The medium can be readily packaged, for example in a membrane such as Parafilm®, as described in detail above. The packaged medium can be sterilized or pasteurized, as desired. The growth medium can be readily freeze-dried and can be used in the freeze-dried form or used after reconstitution with liquid. Techniques for rearing phytophagous arthropods including facultatively zoophagous arthropods are as described above.

Example 2, below, describes the rearing of Lygus on the growth medium of the third embodiment. The new diet surpassed the existing Lygus standard diet (Debolt diet) in terms of productivity, biomass accumulation, and every other biological and economic parameter.

Tests of the new diet of the third embodiment with *L. hesperus* against a control diet consisting of the phytophage diet of U.S. Pat. No. 5,945,271 showed that *Lygus hesperus* reared on the growth medium of the third embodiment developed at rates greater than those reared on the control diet; they produced more eggs per female, had longer survival after reaching the adult stage, and the dry weights of the females and males were significantly greater than those of the control diet.

Further, by use of the growth medium of the third embodiment, for the first time in the history of rearing insects on artificial diets, *L. lineolaris* were reared for multiple generations and with continual increase of biomass. Efforts have been made to rear this insect for the past 40 years with no success until this diet.

Additionally, preliminary tests have shown that lepidopteran larvae (*Heliothis virescens, Helicoverpa zea,* and *Spodoptera exigua*) readily accepted the diet. Fire ants readily accepted the freeze-dried form of the diet.

As a supplement, the diet improved production of the predator *Geocoris punctipes*.

EXAMPLES

The following examples are intended only to further illustrate the invention and are not intended to limit the scope of the invention which is defined by the claims.

Example 1

This example describes an artificial medium of the first embodiment of the invention and its use for rearing larvae of the green lacewing, *Chrysoperla rufilabris*.

The diet ingredients were as follows. The composition of the ingredient listed is given in parentheses:

| | |
|---|---|
| 900 g | chicken eggs, blended (666 g water, 90 g fat, 108 g protein, <9 g carbohydrate) |
| 200 ml | autoclaved tap water |
| 165 g | sucrose (165 g carbohydrate) |
| 30 g | brewer's yeast (12 g fat, 12 g protein, <1 g carbo., approx. 3 g water) |
| 150 g | 50% honey solution (75 g honey mixed with 75 ml water) (113 water, 37 g carbohydrate) |
| 30 ml | 10% acetic acid soln (10 ml glacial acetic acid in 90 ml water) (30 g water) |
| 1475 g | (1012 g water (69%), 102 g fat (6.9%), 120 g protein (8.1%), 212 g carbohydrate (14.4%) |

The diet was prepared as follows: the water, sucrose and honey solutions were boiled. Then the acetic acid and brewer's yeast were added. When all were in a rapid boil, the blended whole eggs were added and stirred constantly until the eggs were a scrambled egg-like mixture.

The growth medium of the invention was used to provide nutrients for rearing the green lacewing, *Chrysoperla rufilabris*. *C. rufilabris* is a highly praised generalist predator. It has been well documented that *C. rufilabris* suppresses populations of aphids, lepidopterans (eggs and small larvae), and a variety of other slow or non-moving, soft bodied arthropods. This entomophage meets the criteria for use as a biocontrol agent such as high kill rates, good search qualities, and proven non-destructiveness to other beneficial arthropods and crop plants.

Tests of the new diet with larval green lacewings were compared to a control diet (U.S. Pat. No. 5,834,177) which consisted of a mixture of ground beef, beef liver, cooked whole egg, water, brewer's yeast, sugar, honey, and acetic acid solution. The diet of the invention produced similar quantities of adults of similar longevity rates, but with slightly lower weights and numbers of eggs. However, the diet of the invention cost less that ⅓ the price of materials and was synthesized in about half the time with about half the labor of the meat paste-based control growth medium. Additionally, the diet of the invention (approx. $0.75/kg) and the meat paste-based control diet (approx. $2.00/kg) produced green lacewings of similar quality and quantity to insect (Ephestia) eggs, which cost about $300–500/kg.

Example 2

The following example illustrates the use of the growth medium of the third embodiment of the invention as an artificial diet for *Lygus hesperus* Knight and *Lygus lineolaris* (facultatively zoophagous phytophages).

The artificial diet for Lygus spp. was prepared as follows:

Component A

Component A comprised the growth medium of the first embodiment with the ingredients prepared as described in Example 1. Component A was made and stored refrigerated in 250 g aliquots.

Component B

The ingredients of Component B were as follows. The composition of the ingredient listed is given in parentheses:

| | |
|---|---|
| 200 g | toasted wheat germ (12 g water, 60 g protein, 23 g fat, 100 g carbohydrate) |
| 300 g | lima bean meal (32 g water, 63 g protein, 3 g fat, 189 g carbohydrate) |
| 50 g | soy flour (4 g water, 17 g protein, 9 g fat, 17 g carbohydrate) |
| 900 ml | tap water |
| 300 ml | egg yolk (153 g water, 91.5 protein, 47 g fat, 3 g carbohydrate) |
| 720 g | (1101 water, 231.5 g protein, 82 g fat, 309 g carbohydrate) |

The ingredients were mixed together and autoclaved for 20 min, 0 dry time. The mixture was allowed to cool to about 50° C.

Component C

The ingredients of Component C were as follows. The composition of the ingredient listed is given in parentheses:

| | | |
|---|---|---|
| 700 ml | water (sterile tap water) | |
| 1 ml | formalin (1 g water) | |
| 10 g | lecithin (with soy oil) (10 g fat) | |
| 8 g | Vanderzant vitamin mixture for insects (ICN 903244)[1] (6 g carbohydrate) | |
| 1 ml | propionic acid (1 gm water) | |
| 0.05 g | chlortetracycline | |
| 0.05 g | streptomycin sulfate | |
| 720 g | (702 g water, 10 g fat, 6 g carbohydrate) | |

The ingredients of Component C were mixed together. Component C and a 250 g aliquot of Component A were added to cooled Component B, and the mixture was mixed in a blender for 4 minutes at medium speed. The completed diet was still warm enough (about 45° C.) to pour as a thick slurry into either storage containers or feeding packets. The ingredients of A plus B plus C totaled 2720 g (72.5% water, 9.3% protein, 4.1% fat, 12.9% carbohydrate). The pH of the mixture was about 5.8.

| [1]Vanderzant Vitamin Mixture | |
|---|---|
| α-Tocopherol | 8 gm/kg |
| Ascorbic Acid | 270 gm/kg |
| Biotin | 20 mg/kg |
| Calcium Pantothenate | 1 gm/kg |
| Choline Chloride | 50 gm/kg |
| Crystalline Folic Acid | 250 mg/kg |
| Inositol | 20 gm/kg |
| Niacinamide | 1 gm/kg |
| Pyridoxine HCl | 250 mg/kg |
| Riboflavin | 500 mg/kg |
| Thiamine HCl | 250 mg/kg |
| Vitamin $B_{12}$ | 2 gm/kg |
| (Trituration in Mannitol) | |
| Q.S. with Dextrose | |

Insects

The *L. hesperus* used in these studies were derived from a colony from Biotactics, Inc. (Riverside, Calif.). They had been colonized at the Gast (USDA, ARS, Biological Control and Mass Rearing Research Unit) facility for 1.5 years using the phytophagous insect diet described in U.S. Pat. No. 5,945,271. The *L. lineolaris* were collected from weeds in Chickasaw County, Miss. Voucher specimens from each colony have been placed in the Mississippi State University Entomology Museum.

Production Set-up

The standard cages used for all life stages were Rubbermaid® 8.3 L rectangular storage boxes, with openings cut into the tops and replaced with 0.4 mm organdy cloth for nymphs or 1.0 mm mesh fiberglass screen for larger nymphs and adults. Rearing room conditions were light: dark cycle of 16: 8 h; temperature of 27° C. (±1.5° C.), and RH 50 to 60%. Cages were placed on racks to allow air circulation and light to reach each cage. The production colony was treated according to the recommendations of Debolt and Patana ("*Lygus hesperus*," pp. 329–338, In *Handbook of Insect Rearing*, Vol. 1, P. Singh and R. F. Moore (eds.), Elsevier Science Publishers B. V. Amsterdam, 1985) except for the modifications specified here. Egg packets were placed intact into cages, rather than being separated from the gel. Egg packets were placed inside cages with shredded paper (0.6× 28.4 cm) rather than loosely wadded paper towels to reduce cannibalism. The first feeding packet provided to newly eclosed nymphs was stretched to facilitate feeding. The colony was kept at 27° C., rather than 26° C. The cages were topped with an organdy cloth held tight by the box's snap-on top that had a 21×30 cm opening. In contrast with the procedures of Debolt and Patana (1985), feeding units were only the cages made from 8.3 L rectangular storage boxes rather than a mixture of cardboard cartons for nymphs and larger feeding units for adults. Using only a single cage reduced the labor and mortality inherent in the extra handling involved in transfer of insects. Finally, a 2%, rather than a 1.2%, gel was used for oviposition. Previous work (Cohen unpublished data) indicated that the higher percentage gel seemed to increase egg hatch.

Experimental Design

To compare the relative effectiveness of each diet, three replicates were set up on Debolt diet (1982) and diet of the third embodiment of the invention. To begin all tests, feeding units were set up consisting of a cage, described above, and inoculated with a Parafilm packet containing approximately 5000 eggs. The packet (about 72 $cm^2$) containing 2.0% Gelcarin® gel (FMC-Food Ingredients Division, Rockland, Me.) was placed in a standard feeding cage (described above). The following parameters were measured for each treatment group: 1) the weight of sexually mature adults, 2) the number and percent of eggs that became adults, 3) the survival of adults 3 w after adult eclosion, 4) the mean biomass (dry weight) accumulated per cage over the total development period and 15 d post adult eclosion, including adults, eggs and deceased nymphs, 5) the mean number of eggs produced by each cage of adults. For egg counts, an Image Pro® Plus image analysis system (Media Cybernetics, Silver Spring, Md.) was used. Means were compared by Student T tests (unpaired or paired, when appropriate) (Sigmaplot). First instar *L. hesperus* were provided with appropriate diet from a packet made of stretched Parafilm® and placed within the cage. After the $1^{st}$ feeding (after 2 d), the standard diet packets were placed on top of the cages every Monday, Wednesday, and Friday. These packets were made with heat sealed, unstretched Parafilm and contained about 10–15 g aliquots of appropriate diet (Debolt and Patana, 1985, supra). To estimate egg production per cage, adults from each feeding regimen were provided with oviposition packets (Patana, *J. Econ. Entomol.* 75:668–669, 1982) daily. Egg packets were made with 2.0% Gelcarin® in tap water and were placed on top of cages as were feeding packets. Oviposition Packets were collected every day, and egg numbers were estimated by counting with the image analysis system mentioned above. The mean number of eggs in 3 randomly selected 3 $cm^2$ areas was multiplied by 24 to correct for the area of the whole packet (72 cm$^2$). Egg packets were collected and counted daily over a 10 d period. Estimates of egg biomass were made by multiplying the numbers of eggs by 18.0, the mean dry weight of individual *L. hesperus* eggs.

Adult weights were measured 4 w after adult eclosion. Samples of 5 adults of each sex from each cage (i.e., 15 males and 15 females per treatment) were weighed to determine the fresh weights. Equal numbers of adults dried for 48 h at 60° C. were used to determine the mean dry weights of individuals from each sex and each treatment. Numbers of adults produced in each cage and survival numbers were estimated from dry weight biomass of surviving and dead individuals harvested at the end of the experimental period. Estimates were made by determination of dry weights of adults (15 from each sex from each treatment). These measurements were made 20 d after adult eclosion.

Results of Comparison to Debolt Diet

Mean biomass production per cage of *L. hesperus* went from 0.09 g (about 5000 eggs) of eggs for each diet treatment to a mean of 7.4 (±0.65) g of adults for the Third Embodiment (TE) diet and 4.6 (±0.46) g of adults for the Debolt diet (T=4.09, P=0.05, DF=2, paired T test), representing increases of 82 and 51 fold, respectively. On a per cage basis, the mean number of individuals that survived until 20 d post adult eclosion (=15 d post onset of oviposition) was 1076 (±102.5) for the TE diet and 625 (±133.3) for the Debolt diet (T=22.3, P=0.002, DF=2). Respectively, for TE and Debolt diet reared *L. hesperus*, mean (±SEM) fresh weights of 1 w post-adult eclosion females were 11.7 (±0.26) and 11.4 (±0.30) mg, and 4 w post-adult eclosion females weights were 11.2 (±0.15) mg and 10.6 (±0.21). Corresponding weights of 1 w adult males were 8.2 (±0.22) and 7.75 (±0.23) mg, and 4 w post-adult eclosion males were 7.9 (±0.21) and 6.7 (±0.18). Dry weights were significantly greater both for females and males on the TE diet, 4.40 (±0.12) and 3.93 (±0.12) for females (T=2.73, P=0.01, DF=28) and 3.09 (±0.08) and 2.57(±0.09) for males (T=4.51, P=0.0001, DF=28), respectively for the TE and Debolt diet treatments. Mean survival to the adult stage was 28.6% for the Debolt diet individuals and 41.8% for the TE diet. A mean of 58.9% (±SD 2.80) Debolt adults remained alive 3 w after adult eclosion compared to 74.4% (±SD 4.16) TE diet adults. The ingredients in the TE diet cost less than ⅛ those used in the Debolt diet and demanded less than ½ of the time required for that diet's preparation.

Discussion

Performance of *L. hesperus* reared on the TE diet was superior to that of subjects reared on the existing standard, Debolt diet, in all biological fitness characteristics measured. This includes biomass accumulation per standard cage (including adults and eggs produced over the life span of a generation. Each cage, started with about 5000 eggs (about 90 mg biomass dry weight), contained roughly 1000 *L. hesperus* adults. By the onset of full reproductive maturity (about 5 d post-adult eclosion), each cage produced between 2000 and 6000 eggs per day with the Debolt diet treatments and between 3000 and 10,000 eggs per day in the TE diet treatments. This resulted in a 51 fold increase biomass accumulation with the Debolt diet treatment and 82 fold increase for the TE treatment.

The greater biomass accumulation in the TE treatment resulted from several factors including a significantly greater egg production, greater weight of individuals, greater percentage of individuals that became adults, and longer survival past the onset of reproductive period (contributing to greater production of eggs). It is important to note that both wet weights and dry weights were greater for TE individuals than for Debolt diet treated *L. hesperus* and that the males were especially impacted by the TE diet treatment.

Comparison to a Second Control Diet

*Lygus hesperus* and *Lygus lineolaris* were reared on the diet of the third embodiment of the invention and growth was compared to those reared on a Control diet consisting of the phytophage diet of U.S. Pat. No. 5,945,271 (a meat paste of ground beef and beef liver mixed with cooked whole chicken eggs, which was mixed together with a comparable plant-based diet of Component B, except the plant-based materials were not supplemented with cooked egg yolk).

Results

*Lygus hesperus* rearing:
  Mean numbers of eggs produced per day:
    Control Diet: 2500–4000 eggs/day/adult cage
    TE Diet: 7000–10,000 eggs/day/adult cage
  Body Weights:
    Control Diet: 10.3 mg for females, 7.6 mg for males
    TE Diet: 11.9 mg for females, 9.5 mg for males
  Biomass Accumulation
    Control Diet: about 2.8 g/cage over 6 weeks
    TE Diet: about 7.5 g/cage over 6 weeks
  Egg Hatch Rate
    Control Diet: 25–45%
    TE Diet: 60–90%
*Lygus lineolaris* rearing:
  Mean Numbers of Eggs/Day
    Control Diet: none
    TE Diet: 8000–10,000 eggs/day/adult cage
  Body Weights:
    Control Diet: none
    TE Diet: 12.5 mg for females, 10.2 mg for males
  Biomass Accumulation:
    Control Diet: none
    TE Diet: about 8–10 g/cage over 6 weeks
  Egg Hatch Rate
    Control Diet: no eggs laid
    TE Diet: 55–80%

Discussion

*Lygus hesperus* reared on the diet of the third embodiment of the invention developed at rates greater to those reared on the control diet; they produced more eggs per female, had longer survival after reaching the adult stage, and the dry weights of the females and males were significantly greater than those of the control diet. A production colony of *L. hesperus* has been maintained on the diet of the third embodiment for over a year and has exceeded 15 generations, with a production scale of about 200,000 per week. About half the eggs from this colony are being used to maintain a colony of about 200,000 parasitoids (*Anaphes iole*, family: Mimaridae; order: Hymemoptera).

Using the diet of the third embodiment of the invention, *Lygus lineolaris* were produced for multiple generations for the first time in the history of insect rearing with artificial diets. Prior to this diet, this species had never been reared beyond a single generation on an artificial diet. It is an extremely difficult insect to colonize, and although it is of great economic and ecological importance as a destructive pest, it has never been reared, even on natural diets, in any substantial enough numbers to be used for biological control programs or other biologically based technologies. The colony is now being produced at a rate of about 50,000 adults/week on the third embodiment of the invention, and there appears to be no biological limitation to the potential production of this species on this diet. No insects of this species were produced using the control diet.

It is understood that the foregoing detailed description is given merely by way of illustration and that modifications and variations may be made therein without departing from the spirit and scope of the invention.

What is claimed is:

1. An arthropod rearing system, which comprises a cage and a growth medium for providing nutrients for rearing caged arthropods which comprises a plant-based phytophage artificial diet in admixture with cooked egg yolk or cooked whole egg, wherein said growth medium is effective for growth of an arthropod, and wherein said growth medium is located within said case or within arthropod-feeding proximity of said cage.

2. The arthropod rearing system of claim 1 wherein said growth medium comprises a slurry comprising 15–45% plant-based phytophage artificial diet plus cooked egg and wherein said nutrients in said growth medium comprise liquid in a total wet weight amount of about 55–85%.

3. The arthropod rearing system of claim 1, wherein said plant-based phytophage artificial diet comprises a plant ingredient comprising meal or flour of beans, grains, seeds or nuts.

4. The arthropod rearing system of claim 1, wherein said growth medium further comprises one or more ingredients selected from the group consisting of lipids, added vitamins, phagostimulatory source, preservative, and antimicrobial agent.

5. A freeze-dried product which comprises a growth medium for providing nutrients for rearing arthropods, which comprises a plant-based phytophage artificial diet in admixture with cooked egg yolk or cooked whole egg wherein said growth medium has been freeze-dried.

6. An arthropod rearing system, which comprises a cage and a growth medium for providing nutrients for rearing caged arthropods, which comprises 5–20% by weight of a mixture essentially free of insect components or meat paste, said mixture comprising cooked egg, carbohydrate source, and liquid and 95–80% by weight of a plant-based phytophage artificial diet which includes cooked egg yolk or cooked whole egg, wherein said growth medium is effective for growth of an arthropod, and wherein said growth medium is located within said cage or within arthropod-feeding proximity of said cage.

7. The arthropod rearing system of claim 6, wherein said plant-based phytophage artificial diet comprises a plant ingredient comprising meal or flour of beans, grains, seeds or nuts.

8. The arthropod rearing system of claim 6, wherein said growth medium further comprises one or more ingredients selected from the group consisting of lipids, added vitamins, phagostimulatory source, preservative, and antimicrobial agent.

9. A freeze-dried product which comprises a growth medium which comprises 5–20% by weight of a mixture essentially free of insect components or meat paste, said mixture comprising cooked egg, carbohydrate source, and liquid and 95–80% by weight of a plant-based phytophage artificial diet which includes cooked egg yolk or cooked whole egg wherein said growth medium has been freeze-dried.

10. The freeze-dried product of claim 9 which is reconstituted subsequent to freeze-drying.

11. The arthropod feeding system of claim 3 wherein one or more of said plant ingredients has been heated.

12. The arthropod feeding system of claim 7 wherein one or more of said plant ingredients has been heated.

13. A covered or packaged growth medium for providing nutrients for arthropods in-covered or packaged form, which comprises an insect phagostimulant membrane and an arthropod growth medium comprising a plant-based phytophage artificial diet in admixture with cooked egg yolk or cooked whole egg, wherein said insect phagostimulant membrane covers or encloses said growth medium, and wherein said covered or enclosed growth medium is effective for growth of an arthropod.

14. A covered or packaged growth medium for providing nutrients for arthropods in covered or packaged form, which comprises an insect phagostimulant membrane and an arthropod growth medium comprising 5–20% by weight of a mixture essentially free of insect components or meat paste, said mixture comprising cooked egg, carbohydrate source, and liquid and 95–80% by weight of a plant-based phytophage artificial diet which includes cooked egg yolk or cooked whole egg, wherein said insect phagostimulant membrane covers or encloses said growth medium, and wherein said covered or packaged growth medium is effective for growth of an arthropod.

* * * * *